(12) United States Patent
Murkin

(10) Patent No.: US 6,248,072 B1
(45) Date of Patent: Jun. 19, 2001

(54) HAND CONTROLLED SCANNING DEVICE

(76) Inventor: John M. Murkin, 106 Oxford Street West, London (CA), N6H 1R9

( * ) Notice: Subject to any disclaimer, the term of this patent is extended or adjusted under 35 U.S.C. 154(b) by 0 days.

(21) Appl. No.: 09/296,417

(22) Filed: Apr. 23, 1999

Related U.S. Application Data

(63) Continuation-in-part of application No. 09/156,504, filed on Sep. 19, 1998.
(60) Provisional application No. 60/059,565, filed on Sep. 19, 1997.

(51) Int. Cl.[7] .................................................. A61B 8/00
(52) U.S. Cl. ................................................................ 600/446
(58) Field of Search ........................................ 600/437, 439, 600/442, 443, 447, 449, 456, 462, 446; 601/2, 3; 604/119; 358/98; 364/413.13

(56) References Cited

U.S. PATENT DOCUMENTS

| | | | |
|---|---|---|---|
| 4,667,230 | * 5/1987 | Arakawa et al. | 358/98 |
| 5,016,173 | * 5/1991 | Kenet et al. | 364/413.13 |
| 5,270,810 | * 12/1993 | Nishimura | 358/98 |
| 5,413,107 | * 5/1995 | Oakley et al. | 600/462 |
| 5,476,090 | * 12/1995 | Kishi | 600/121 |
| 5,598,846 | * 2/1997 | Peszynski | 600/462 |

* cited by examiner

Primary Examiner—Francis J. Jaworski
Assistant Examiner—Ali M. Imam
(74) Attorney, Agent, or Firm—Bereskin & Parr

(57) ABSTRACT

A hand held imaging probe for use by a surgeon as a diagnostic tool is described. The probe is held and operated in one hand by the surgeon independent of any other operator. The probe incorporates either finger button switches or a thumb wheel rocker switch to adjust a variety of parameters associated with visual images generated from the ultrasonic probe. Also described is a method for producing ultrasonic images by a single operator through a hand held and operated ultrasonic probe. Alternative embodiments which incorporate an aspirator and offset device are also described.

23 Claims, 7 Drawing Sheets

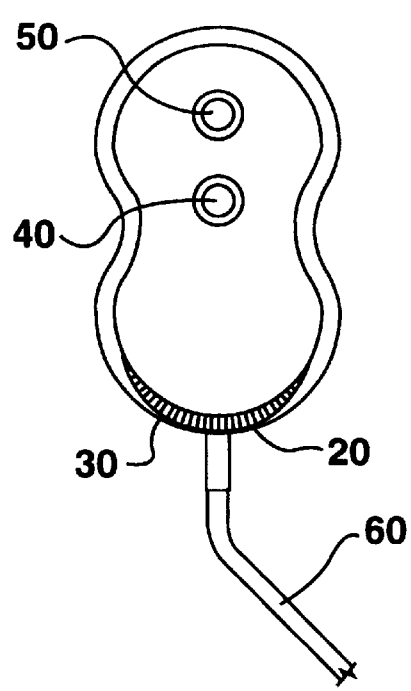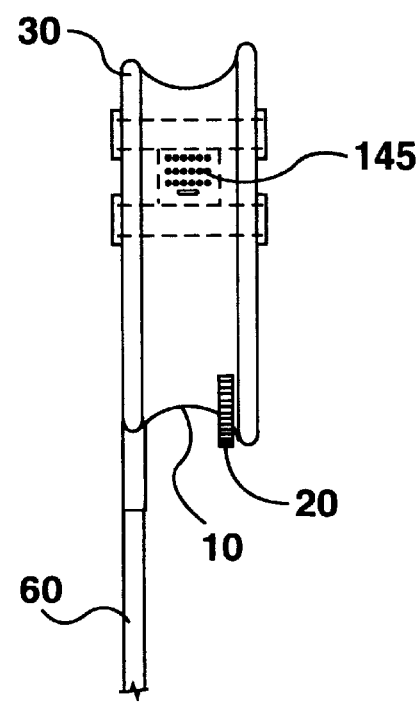
FIG. 2  FIG. 1

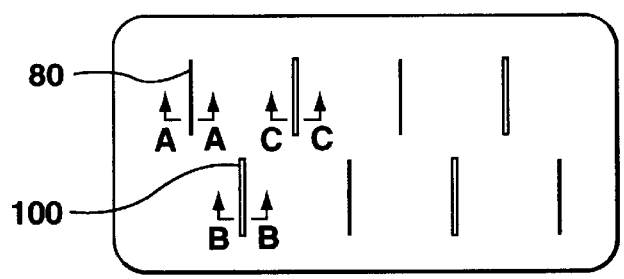
FIG. 4  FIG. 5
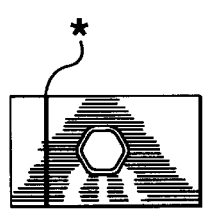 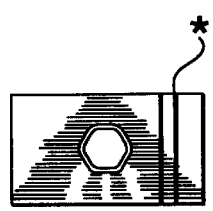 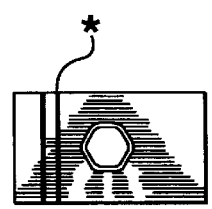
FIG. 6  FIG. 7  FIG. 8

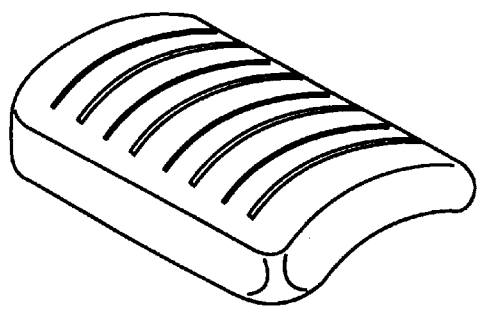
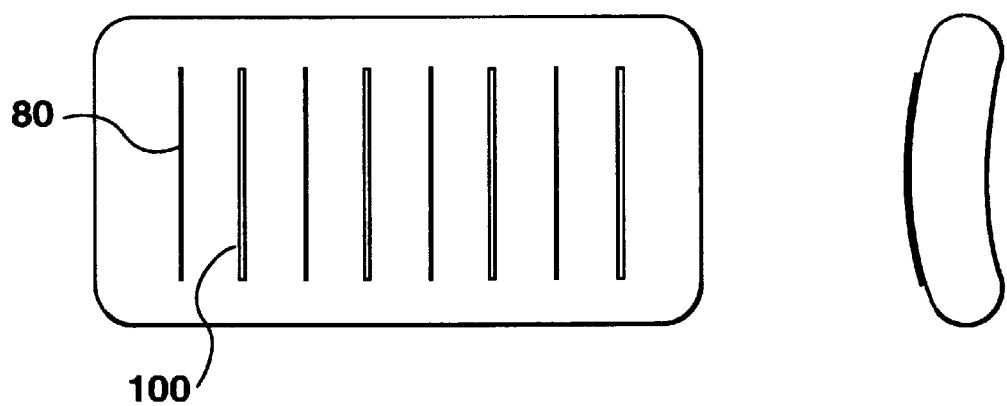
FIG. 9

HAND CONTROLLED SCANNING DEVICE

This application claims benefit from U.S. provisional application Ser. No. 60/059,565 filed on Sep. 19, 1997 and is a continuation-in-part of U.S. application Ser. No. 09/156,504, filed Sep. 19, 1998.

FIELD OF INVENTION

This invention relates to the field of diagnostic surgical tools, and more particularly relates to a device utilizing ultrasound for diagnostics.

BACKGROUND OF THE INVENTION

Stroke Risk After Cardiac Surgery

An estimated 330,000 surgical procedures were performed using cardiopulmonary bypass (CPB) in 1994 in the United States (Mills, 1995). With the increasing age and incidence of concomitant disease, it is increasingly recognized that emboli from instrumentation of an atherosclerotic aorta is an important source of stroke and central nervous system (CNS) morbidity (Murkin et al., 1995; Blauth et al., 1992; and Tuman et al., 1992). There is a direct correlation between age, peripheral vascular disease, and insulin dependent diabetes mellitus (IDDM) and severe atherosclerosis of the ascending aorta and atheroemboli production (Blauth et al., 1992). In a large postmortem study of 221 patients dying after cardiac surgery, atheroemboli were present in the brains in 37% of patients with severe disease of the ascending aorta but only 22% of the patients without severe disease (Blauth et al., 1992). 95% of patients who had evidence of atheroemboli postmortem (and would have manifested all the signs of a stroke had they lived), had severe atherosclerosis of the ascending aorta (Sylviris et al., 1997). In a study of 2000 CAB patients, Tuman et al, (1992), reported an overall postoperative stroke rate of 2.8%, but in patients 65 to 74 it was 3.6%, and in those over age 75 the stroke rate was 8.9%. Currently 30 to 40% of the population we operate upon for coronary bypass surgery is in this age range. Patients with a postoperative neurologic event had a nine-fold increase in mortality (35.7% versus 4.0%).

Current Detection of Aortic Plaque

In fewer than 50% of patients can the presence of aortic arch atheromatous disease be predicted preoperatively using chest X-ray (CXR), or aortogram (Hosoda et al., 1991). Furthermore, 50–80% of significant atherosclerotic lesions in the ascending aorta are missed by intra-operative palpation by the surgeon (Hosoda et al., 1991; Davila-Roman et al., 1994; Barzilai et al., 1989; Marschall et al., 1989; and Katz et al., 1992). Katz et al., (1992), found that in a prospective study involving 130 patients, 19 (83%) of 23 patients with severe disease by TEE were graded normal or mild by palpation. While calcific aorta can be assessed reasonably well, "Cheesy" atherosclerosis is extremely difficult to detect by palpation (Landymore and Kinley, 1983). Manual palpation of the aorta by the surgeon to assess for optimal cannulation sites is currently the standard of care in most cardiac surgical centers in North America. Identifying severe aortic disease has important clinical implications because surgical technique, including aortic cannulation to connect to the heart-lung machine (cardiopulmonary bypass, CPB machine) and anastomosis of proximal coronary grafts, and other such interventions may be altered or relocated to avoid areas of atherosclerotic plaque and should reasonably result in a decrease in stroke rate and in mortality associated with patients undergoing cardiac surgery (Hosoda et al., 1991; Davila-Roman et al., 1994; Barzilai et al., 1989; Marschall et al., 1989; Katz et al., 1992; and Wareing et al., 1992)

Intraoperative Aortic Scanning

Rather than manual palpation, intra-operative ultrasound studies of the aorta using transesophageal echocardiography (TEE) of the aorta has been recommended as a routine in order to detect aortic atherosclerosis and guide surgical cannulation etc (Hosoda et al., 1991). However, 1) this is an expensive instrument (average $125,000–$500,000 capital cost), 2) requiring significant expertise and an independent dedicated operator (presence of a dedicated technician or specially trained physician) for its intraoperative usage, and 3) its ability to detect all aortic arch lesions has been questioned since the air-tissue interface resulting from the lung and trachea prevents the identification of lesions in the upper ascending aorta and the aortic arch, where cannulation is done (Seward et al., 1990; Konstadt et al., 1994; Sylviris et al., 1992; and Kanchuger et al., 1994).

Alternatively, employment of a hand-held epiaortic B-mode scanning probe has been shown to be more efficacious than TEE and similarly alters the site of aortic cannulation and instrumentation in 20–24% of CPB cases (Barzilai et al., 1989; Ohteki et al., 1990; and Davila-Roman et al., 1991). Epiaortic B-mode scanning has been shown to be accurate to assess severity and location of atherosclerosis of the ascending aorta and allow modification of the standard technique for cannulation by choosing a safer site (Davila-Roman et al., 1994 and Wareing et al., 1992). Epiaortic scanning has been found to more reliable in identifying plaque in the distal ascending aorta where TEE is less helpful. Katz and colleagues (1992) showed that all 5 patients in whom severe distal ascending plaque was found by direct epiaortic probe were missed by biplanar TEE. The use of this instrument would obviate the need for manual palpation of the aorta, in itself a cause of embolization (Karalis et al., 1992).

Currently the standard of care continues to be visual inspection and palpation of the aorta by the surgeon, despite the fact that it has been shown to identify atheromatous disease in only 25–50% of patients and even then underestimates atherosclerotic severity compared with ultrasound scanning (Seward et al., 1990; Konstadt et al., 1994; Sylviris et al., 1992; and Kanchuger et al., 1994).

A further problem relates to the inability to reliably remove air and particulate debris from within the heart after open-heart surgery (valvular surgery, septal defect repairs, congenital heart surgery) because of an inability of the surgeon to view the interior of the heart chambers. Current techniques employ blind needle aspiration of the heart chambers which is unreliable for effective removal of such foreign matter. Use of TEE enables visualization of air/debris within the heart chambers but does not assist with localization of the tip of the aspirating needle since it is introduced from a separate site. Thus the needle aspiration is performed 'blindly' and is only randomly in contact with air within the heart cavity.

Traditional medical ultrasound devices are not designed to be operated and controlled from within a sterile surgical field. They are designed to be controlled and run by an external operator (technician) with the surgeon acting to position the probe within the surgical field. Accordingly they require ancillary support personnel who must respond to input from the surgeon or other individual manipulating the probe in the operative field in order to obtain the best images of the tissue under study. Further, current medical ultrasound devices are relatively large machines designed for a variety of other imaging applications, generally external to the body. In the restricted space of the operating room, this large size is potentially hazardous as it may block access to the patient or other necessary medical equipment. There are smaller general purpose ultrasound devices, but they have a very small display and are designed to be viewed at close range. They are thus rendered difficult to see when viewed from within the operating field and they also cannot be controlled from within the surgical field.

Because of a multiplicity of uses traditional medical ultrasound devices are complex to operate and require the presence of a trained technician. Additionally, the imaging controls are located on the nonsterile housing of the ultrasound device. Thus, an operator is not able to control the ultrasound scanning device independently from within the sterile surgical field.

A related problem associated with current scanning devices is that scanning probes placed directly on tissue often results in a loss of near field resolution. Use of gel offsets have been employed to enhance near field resolution, however, this has resulted in an inability to identify the location of the tissue being imaged with precision, due to the opaque nature of gel offsets. Furthermore, in this respect, there is currently no ability to precisely orient a scanned image with respect to anatomical features of tissue which is being imaged.

SUMMARY OF THE INVENTION

The imaging device of the present invention is a hand held imaging probe for use as a diagnostic tool by an individual where the probe is held and operated in one hand by the individual. The probe comprises a tissue contacting section which contains one or more elements capable of sending and receiving one or more signals to and from the tissue. It also has a means for coupling the signals with a signal processor; means for generating images of the tissue from processed signals from the signal processor; and means in the probe for controlling by a digit of the individual at least one parameter of the image. More particularly, all parameters for imaging are controlled by the surgeon from the operating field.

The present invention also includes a method for producing an ultrasonic image of the interior of vasculature comprising: i) contacting an ultrasonic transducer section of a hand held intraoperative ultrasonic imaging probe to the vasculature; ii) causing the transducer to send and receive one or more signals to and from the vasculature; iii) coupling the signals with a signal processor; iv) displaying at least one image of the interior of the tissue generated from processed signals from the signal processor; and v) controlling by a thumb of a surgeon through a thumb wheel rocker switch at least one parameter of the image, thereby enabling the surgeon to control all functionality from the operating field.

The device is preferably an intra-operative ultrasound (U/S) device specifically designed for use as a diagnostic surgical tool by a surgical operator independent of the need for any external technician support.

The ultrasound probe of the present invention provides a two-dimensional high resolution cross-sectional image of tissue which is being scanned. According to a preferred embodiment, the tissue being scanned is the aorta, particularly to provide images of the aorta and other vascular structures. However as will be appreciated by those skilled in the art, this device is not limited to only aortic tissue.

The ergonomics of the probe design and of the image display, combined with the sterile field-based location of control features provide an imaging device specifically suited for use by a surgical operator.

More particularly, the ergonomic finger group probe design incorporates push button controls enabling each image capture to be at the finger touch control of the surgical operator. According to a preferred embodiment the controls are located on a wrist-mounted unit with means to hold a probe which does not itself have any control features. However, although this is a preferred embodiment, whether the functionality of the probe is controlled from switches on the probe, on a wrist or forearm mounted unit or otherwise, it is understood that all means by which control over all parameters of the image, including anterior field resolution, gray scale, image capture, device on/off, Doppler/B-mode switching, on-screen cursor control for edge delineation, are brought under the control of the surgeon within the surgical field, are within the scope of the present invention.

According to a further aspect of the present invention, a saline-filled de-aerated and acoustically and visually transparent crescent shaped offset is utilized in association with the ultrasound scan probe of the present invention.

According to one aspect of the ultrasound scanning device of the present invention, there is incorporated a near infrared spectra scope (NIRS) scan which is incorporated into the probe housing and can be used to identify both tissue structure and tissue composition.

According to a further embodiment, the probe design is based on a minimal height probe with ergonomically correct "grooves" located in the sides of the probe for finger placement. According to a further embodiment of the present invention, a thumb wheel rocker switch enables images to be captured and stored by the independent surgical operator.

According to one further modification, the ultrasound transducer, preferably an ultrasound crystal, can function alternately in "Doppler" mode or "B-mode". In Doppler mode, flow velocity (FV) in a blood vessel is measured. In B-mode, the cross-sectional area (Area) of the blood vessel is measured.

According to a further modification, an ultrasound transducer may be coupled to an aspiration tube, preferably silastic tubing capable of atraumatic insertion into the chambers of the heart. Incorporation of an ultrasound probe fixed to a hollow aspiration tube which can be passed as a combined unit atraumatically across the heart valves, locates the tip of the aspiration device in direct proximity to the ultrasound beam. All air or debris which is located by the ultrasound beam is thus able to be aspirated directly under ultrasound guidance from within the heart.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

DESCRIPTION OR THE DRAWINGS

The invention will now be described in relation to the drawings in which:

FIG. 1 provides a simplified side view of a scanning probe of the present invention.

FIG. 2 provides a top plan view of the scanning probe of FIG. 1.

FIG. 3 provides a block diagram of an ultrasound imaging system that incorporates a preferred embodiment of the present invention.

FIG. 4 provides a top plan view of a saline-filled offset of the present invention.

FIG. 5 provides a side view of the offset of FIG. 4.

FIG. 6 provides a further top plan view of a different embodiment of the offset of FIG. 4.

FIG. 7 provides a cross-sectional view illustrating the transmission of sonic waves through tissue around an aorta.

FIG. 8 represents an alternative view in connection with the image provided at FIG. 7.

FIG. 9 provides a further view of the image in connection with the subject matter of FIG. 7.

FIG. 10 provides a view of an endocavitary ventricular aspirator coupled with an ultrasound probe of the present invention.

DETAILED DESCRIPTION OF THE INVENTION

Figure 3:
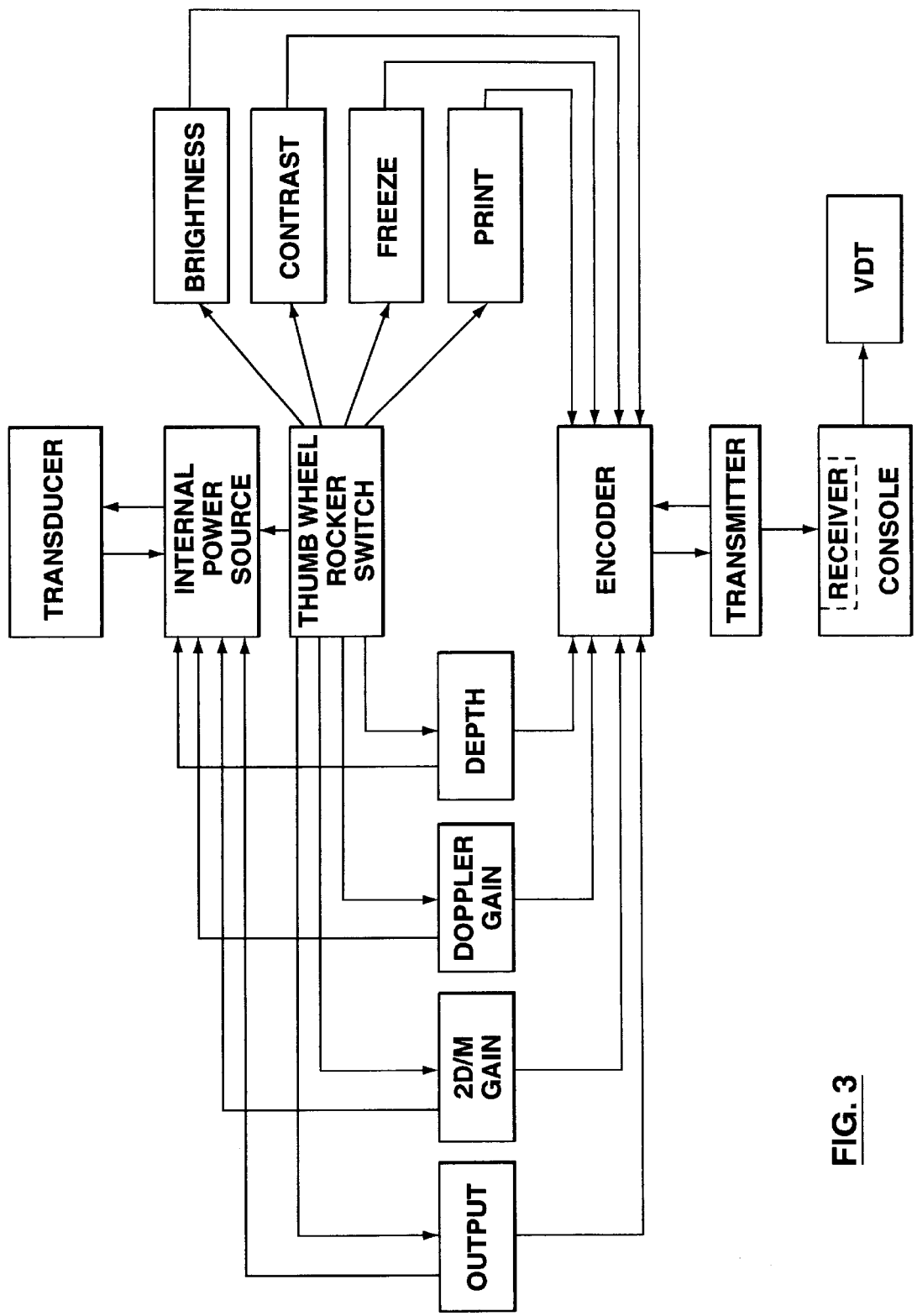

The ultrasound scanning device I have invented is unique in concept and design. The device consists of four components: one being a high resolution, large screen, digital, flat panel display; another being a low-profile, ergonomically designed ultrasound probe incorporating a control device to initiate image capture and storage; the third being a transparent scanning probe offset incorporating an acoustically dense grid to facilitate scan image localization.

Current devices employed for epiaortic scanning or other such intraoperative, intracavitary imaging applications are not designed for use primarily within the body via a surgical incision. Accordingly, they are much bulkier devices designed for a wide range of applications but their use is generally confined to scanning from outside the body. This multiplicity of operations renders them complex to operate and expensive to purchase and maintain. The majority of other ultrasound devices also require the continuous presence of a trained technician in order to operate them. The scanning probes are generally large and bulky and are not designed for use within the body. Other, smaller ultrasound devices are also fundamentally different in nature in that they are designed to be viewed at close range and thus they do not incorporate a large screen display. This renders them difficult to see when viewed by an operator from within the surgical field. Similarly they do not employ ultrasound probes designed for use directly within the body. My scanning system incorporates a high resolution large screen digital flat panel display that can be easily mounted on any surface within the operating field. The very small physical size of this display unit makes it unobtrusive yet easy to see by the surgeon from within the surgical field.

My ultrasonic scanning probe is designed to be employed by the operator and used to initiate image capture and storage. My probe has finger switches for these purposes enabling it to be readily held and controlled by a user wearing surgical gloves. According to an alternative embodiment, the switches are located on a wrist-mounted unit which is capable of being controlled by the operator in the surgical field, and provides means to place the probe on the unit allowing the operator (surgeon) to have freedom of use of both hands.

Accordingly, the present invention provides a hand held imaging probe for use as a diagnostic tool by an individual where said probe is held and operated in one hand by the individual, said probe comprising:

i) a tissue contacting section containing one or more elements capable of sending to and receiving from said tissue one or more signals;

ii) means for coupling the signals with a signal processor;

iii) means for generating images of the tissue from processed signals from the signal processor; and iv) means in the probe for controlling by at least one digit of the individual at least one parameter of the image. Preferably the probe is an intraoperative ultrasonic probe and the elements are ultrasonic transducers and the tissue is the aorta. More preferably the individual is a surgeon. The means for controlling the signals, may be according to one embodiment a series of finger activated switches which correspond to one or more parameters selected from the group consisting of 2D/M gain, Doppler gain, depth, output, brightness, contrast, freeze or print.

Preferably the means for controlling the signals is a thumb wheel rocker switch to control one or more parameters selected from the group consisting of 2D/M gain, Doppler gain, depth, output, brightness, contrast, freeze or print. According to another embodiment the means for coupling the signals with the signal processor is wireless. The ultrasound transducers of a preferred probe can function alternately in Doppler or B-mode.

The invention may also provide that the probe is coupled to an aspiration tube capable of atraumatic insertion into the chambers of the heart, preferably the tube is silastic tubing. According to one embodiment a scanning probe offset is located between the surface of the probe which contacts tissue and the tissue, preferably the offset is saline-filled and has an acoustically dense grid.

The present invention also provides a hand held imaging intraoperative ultrasonic probe for use by a surgeon as a diagnostic tool where said probe is held and operated in one hand of the surgeon, said probe comprising:

i) a tissue contacting section containing one or more ultrasonic transducers capable of sending to and receiving from the tissue one or more signals;

ii) means for coupling the signals with a signal processor;

iii) a video display terminal for generating images of the interior of the tissue from processed signals from the signal processor; and iv) means in the probe for controlling by a digit of the surgeon at least one parameter of the image. Preferably the means for controlling is a thumb wheel rocker switch which controls 2D/M gain, Doppler gain, depth, output, brightness, contrast, freeze and print functions.

According to another aspect, the present invention provides method for producing an ultrasonic image of the interior of vasculature comprising:

i) contacting an ultrasonic transducer section of a hand held intraoperative ultrasonic imaging probe to the vasculature;

ii) causing the transducer to send to and receive from the vasculature one or more signals;

iii) coupling the signals with a signal processor;

iv) displaying at least one image of the interior of the vasculature generated from processed signals from the signal processor; and v) controlling by controlling means of the probe at least one parameter of the image. Preferably the vasculature is the aorta and the parameter is selected from the group consisting of 2D/M gain, Doppler gain, depth, output, brightness, contrast, freeze or print.

An embodiment of the method provides controlling means selected from the group consisting of a thumb wheel rocker switch and individual finger switches, preferably the signals are coupled with the signal processor by a wireless connection.

According to another embodiment of a method of the invention the probe is coupled to an aspiration tube capable of atraumatic insertion into the chambers of the heart. Preferably the method is practised where a scanning probe offset is located between the surface of the probe which contacts tissue and the tissue and the offset is saline-filled and has an acoustically dense grid on its surface.

According to yet another embodiment of the invention there is provided a hand held imaging probe for use as a diagnostic tool by an individual where said probe is held in one hand by the individual, and is controlled through a unit attached to the individual, said unit comprising:

i) means for coupling signals from the probe with a signal processor;

ii) means for generating images of the tissue from processed signals from the signal processor; and iii) means in the unit for controlling by at least one digit of the individual at least one parameter of the image.

Scanning Probe

Referring now to FIG. 1, there is provided a view of a probe of the present invention with appropriate grooves 10, located at the sides for comfortable placement of the operator's fingers. A thumb control 20 (which is described in greater detail below) is located at the rear of the probe 30. Thumb wheel rocker switches are well known in the art, see for example U.S. Pat. No. 4,502,050 by Hibi which teaches a position discrimination device for a thumb wheel switch. Control buttons invoking the near infrared spectra scope scan and tissue composition scan are located conveniently on the top surface of the probe 30 at positions 40 and 50 respectively. Alternatively, other finger buttons can be incorporated as an array across the surface of the probe replacing the thumb control yet providing similar functionality.

In this respect each button provides a signal to a signal processing unit for each modality over which control is exerted. According to a preferred embodiment there is a switch for 2D/M gain, Doppler gain, depth, output, brightness, contrast, freeze and print. A separate finger (preferably the thumb) switch is located on the side of the probe signals from which adjust the value up or down of the modality under review by the operator, such as for example the 2D/M gain. As will be understood by those skilled in the art, the 2D/M gain switch controls the overall amount of amplification or gain applied to signals produced by echoes returning from the tissue being scanned. The Doppler gain switch adjusts the amount of amplification or gain applied to Doppler signals returning from the tissue under examination. The finger switch for depth control adjusts the actual depth range of the display. The amount of depth which can be achieved will depend upon the nature and character of the ultrasound transducers employed. The output switch controls the acoustic power output which is interpreted as intensity spatial peak time average derated and mechanical index for display. The freeze button stops or starts all display updates and data acquisition while the print button initiates a print of the video monitor display on whatever hardcopy device is coupled to the entire apparatus.

As shown in FIG. 1, a connecting medium such as a cable 60 couples the probe to an external signal processing and display unit (not shown). In a preferred embodiment, the image display is light weight, employs a high resolution colour flat panel video screen, and can be mounted on an IV pole. The display is capable of adjustment and viewing from the surgical field.

In an alternative arrangement, the coupling medium consists of a communications circuit which includes a transmitter and antenna. A receiver and antenna are built into the signal translation/video display unit to allow for wireless communication between the probe and the processing/display unit. In a preferred embodiment, signal transmission would be SST or digital although conventional radio wave transmission may be used.

In the embodiment wherein control over different modalities is exerted through use of a thumb control rocker switch, activation of the switch provides the operator with an on-screen menu displaying the choice of modalities referred to above, eg., 2D/M gain, Doppler gain, etc. Rotation of the wheel allows the user to select the desired modality and subsequent depression of the switch "chooses" the modality. Once the modality is chosen, the operator is provided with a further menu or range, etc, by which rotation of the thumb wheel switch either increases or decreases the chosen modality. Referring to the block design diagram in FIG. 3 it may be seen that transducer element position is adjusted depending upon the image obtained as seen by the operator on the video display terminal or VDT in response to changes entered via the thumb control rocker switch in connection with 2d/M gain, Doppler gain, depth and output. Each movement is encoded and a signal transmitted to the receiver contained in the console for display on the VDT.

Figure 11:
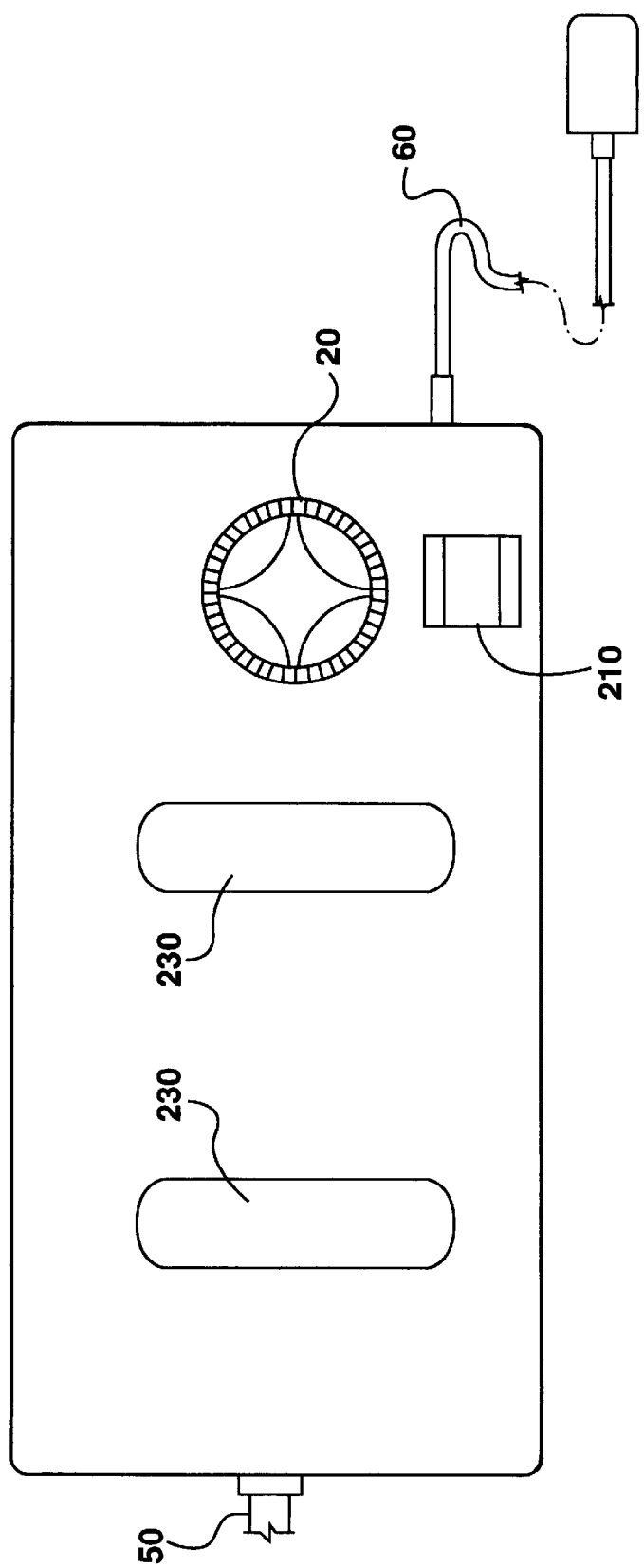
FIG. 11 illustrates a top plan view of a wrist-mounted controller of the present invention.
Figure 12:
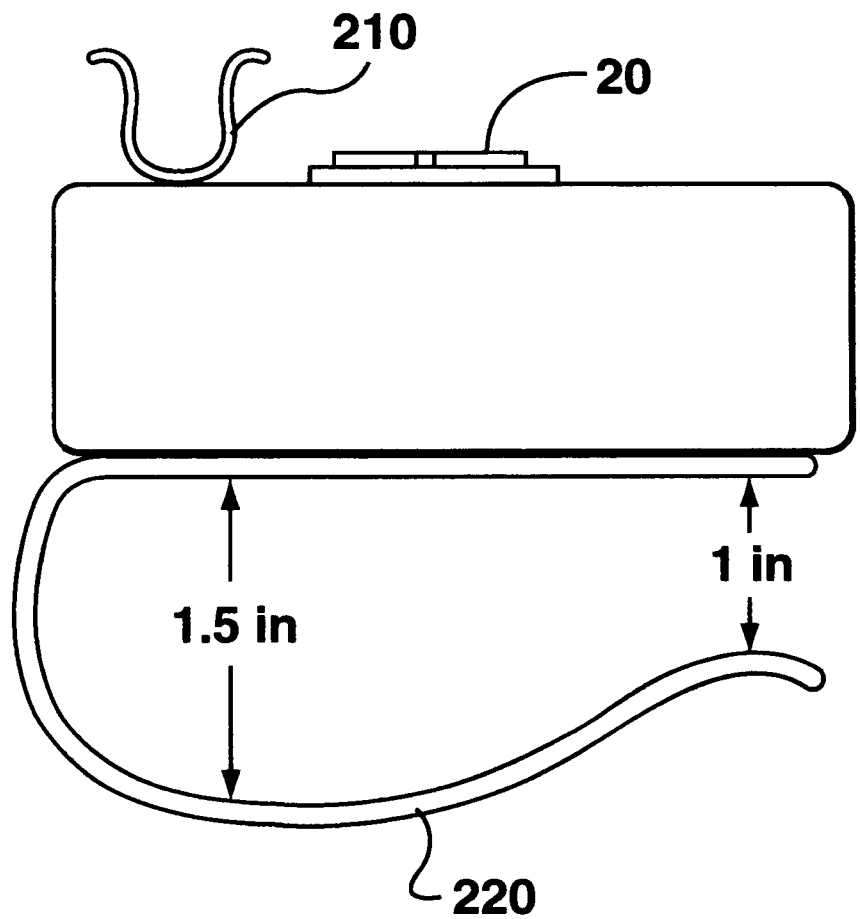
FIG. 12 illustrates a side view of the wrist-mounted controller of FIG. 11.

According to an alternative embodiment the probe does not have control switches (see FIG. 11), rather, they are located on a unit as depicted in FIGS. 11 and 12. Referring now to FIG. 11, on/off and select switches 230 are located to one side of the unit while a thumb rocker switch 20 is located adjacent these switches. The rocker switch in this embodiment provides the user with similar or the same control over the modalities described in respect of the switch on the probe. Control over different modalities is exerted through use of this thumb control rocker switch much as previously described, namely, activation of the switch provides the operator with an on-screen menu displaying the choice of modalities referred to above, eg., 2D/M gain, Doppler gain, etc. Rotation of the wheel allows the user to select the desired modality and subsequent depression of the switch "chooses" the modality. Once the modality is chosen, the operator is provided with a further menu or range, etc, by which rotation of the thumb wheel switch either increases or decreases the chosen modality. Although not shown, the modalities may be accessed through a series of button switches on the surface of the unit.

Also on the unit is a flexible probe holder 210, which allows the surgeon to place the probe in a convenient accessible location at any time during surgery two hands are required. In a preferred embodiment the probe holder is a soft plastic material although any suitable material may be used. Attached to the surface opposite the control switch side a holder which permits easy, but secure, attachment and removal of the wrist unit is provided 220. A cord 50 to the ultrasound display and a cord 60 from the unit to the probe are provided. It will be appreciated that wireless communication between the wrist-mounted unit and the display panel is also contemplated, as is wireless communication between the probe and the wrist-mounted unit.

The ultrasound transducer is, in a preferred embodiment, a composite array of individual ultrasonic transducers adapted to transmit ultrasonic probing signals into living tissue and to receive reflected signals according to principles well known in the prior art such as those taught in U.S. Pat.

No. 4,409,838 by Schomberg, and which have been subsequently improved upon this art. The transducer functions alternately in "Doppler" mode or "B-mode". In Doppler mode, flow velocity (FV) in a blood vessel is measured. In B-mode, the cross-sectional area (Area) of the blood vessel is measured. These determinations are standard, software derived parameters obtained from ultrasound scanning probes and are well known in the prior art. See for example Hossack (U.S. Pat. No. 5,769,079). In summary, by calculating the product of mean flow velocity and cross-sectional area, flow in milliliters per minute can be derived according to the equation:

$$FV(cm/sec) \times Area(cm^2) = Flow\ (cc/sec)$$

This will enable determination of the flow within the coronary artery and any other blood vessel being scanned to be readily determined by the operator.

The brightness, contrast, freeze and print control signals (FIG. 3) generated by the user through activation of the thumb control rocker switch operate to adjust the VDT directly at the console without input to the transducer. In this way the probe of the present invention operates both as an input device to pure VDT display features (eg. brightness) and as an operator of transducer position which has reporter feedback functionality as well as signal generation based on received echos, all of which, in combination, in the operator's probe, give the surgeon control over the image generation and capture.

Scanning Probe Aspirator

Figure 10:
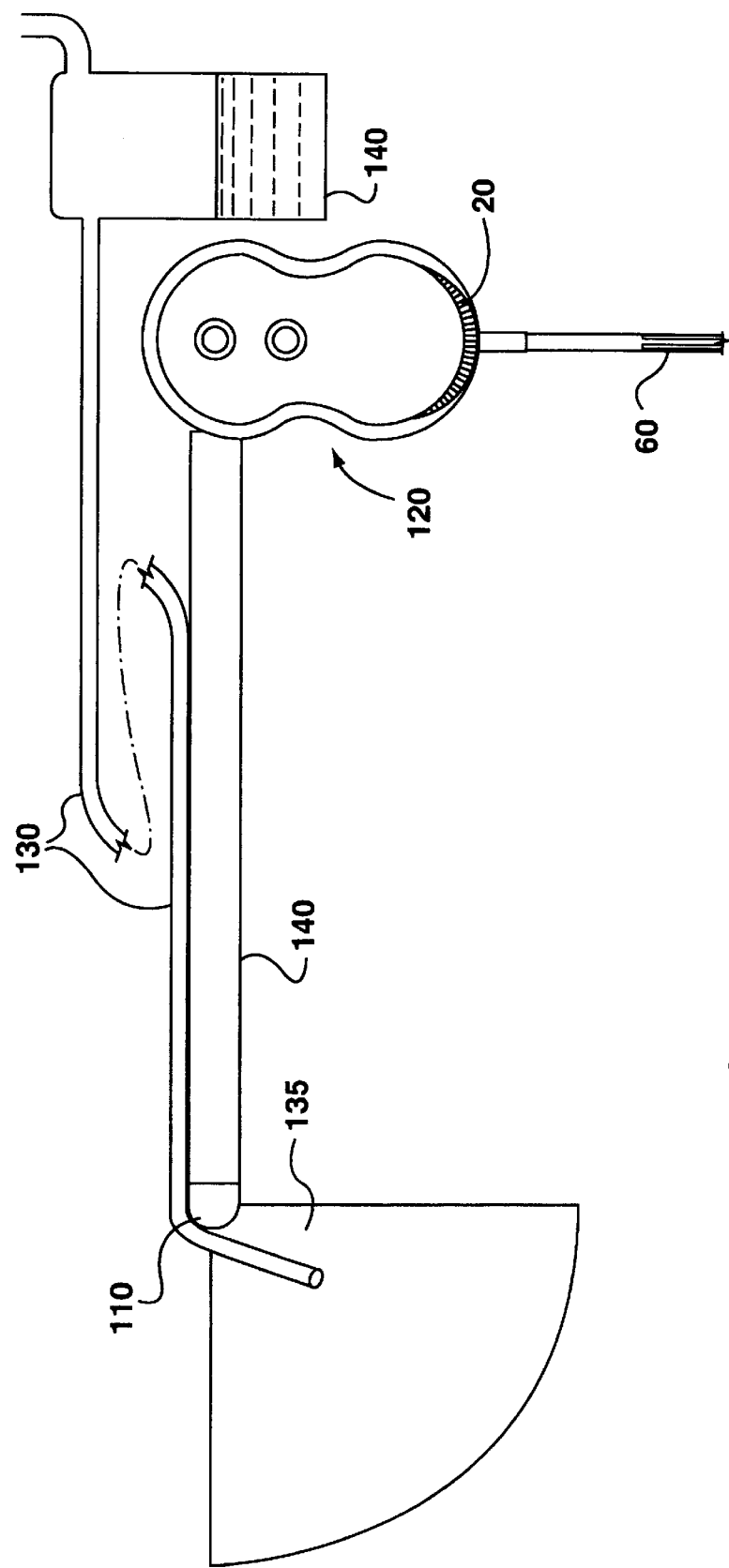

In another embodiment of the present invention, an ultrasound transducer is mounted on a narrow tube designed for atraumatic insertion via the surgeon into the chambers of the heart. Referring to FIG. 10 it may be seen that the transducer portion (110) of the probe has been incorporated into the end of a rigid arm adaptor (140) which, as may be seen in FIG. 1, fits into a connecting port (145) on the left side of a probe of the present invention (120). A standard long rigid arm probe may also be used in this application. A disposable preformed curved silastic tubing (130) is attached to the rigid arm by any standards means, including tying, use of an elasticized ring, or other such measures as will be readily apparent to those skilled in the art. The position of the tubing is such that the aspirating end is located within the scan sector of the ultrasound transducer (135). The other end of the aspirator tubing is attached to a blood/air trap (140) which is in turn attached to a vacuum source (not shown). Incorporation of the air/blood aspiration tubing oriented coincident with the beam of the ultrasound transducer enables detection and aspiration of air and debris from within the chambers of the heart. This device and procedure will reduce the likelihood that any such material will remain within the heart and be ejected from the heart after the operation, thus reducing the attendant risk of stroke.

Scanning Probe Offset

The scanning probe offset, is transparent and is a saline-filled sterilizable bag that incorporates an acoustically dense grid to facilitate scan image localization. It is comprised of 0.9% saline contained within a biologically inert, sterilizable, transparent polyvinyl chloride capsule that has been de-aerated to eliminate microbubbles even upon agitation. The offset is a low pressure design which is readily deformable. De-aeration renders this offset acoustically neutral, unlike other possible devices such as commercially available intravenous solution. A saline-filled sterilizable bag that incorporates an acoustically dense grid to facilitate scan image localization.

The incorporation on the surface of the offset of an acoustically dense grid comprised of a double row of alternating single or double lines, which will be seen upon scanning alternately on the right or left side of the viewing screen, enables the location of atheromatous material identified within the aorta or blood vessel being scanned to be correlated with the external surface of the aorta or blood vessel.

Referring now to FIGS. 4, 5 and 6, there may be seen a saline-filled offset of the present invention, wherein a first embodiment (FIG. 4) single (80) and double (100) acoustic lines are used at regular spacing. This acoustically dense grid registers a signal on the screen of the ultrasound scan probe of the present invention which is coincident with the scanned image corresponding to a specific point on the grid. This enables the scanning image to be referenced to a specific anatomical location.

An alternative embodiment of the offset is illustrated in FIG. 6 and the aforementioned regularly spaced acoustic lines can be incorporated in alternate sides as shown in FIG. 6.

FIGS. 7, 8 and 9, represent the images seen on the scanner viewing screen when an aorta is being scanned through the scan probe offset. In all three figures the central circular image represents the aorta being scanned, and show it being outlined within the triangular shaped ultrasound beam. The single dense line to the left of the image on FIG. 7, the double dense lines to the right of the image on FIG. 8 and the double dense lines to the left of the image on FIG. 9, represent the ultrasonic "shadow" cast by the scanner as it moves across the acoustic lines on the scan probe offset.

As will be appreciated by those skilled in the art the present invention is readily applicable for imaging any vascular structure that is accessible from the surgical field and is in no way limited to the aorta.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

FULL CITATIONS FOR REFERENCES REFERRED TO IN THE SPECIFICATION

1. Mills S A. Risk factors for cerebral injury and cardiac surgery. Ann Thorac Surg 59:1296–9, 1995.
2. Murkin J M, Martzke J S, Buchan A M, Bentley C, and Wong C J. A randomized study of the influence of perfusion technique and pH management strategy in 316 patients undergoing coronary artery bypass surgery. II) Neorologic and cognitive outcomes. J Thorac Cardiovasc Surg 110:349–62; 1995.
3. Blauth C I, Cosgrove D M, Webb B W, Ratliff N B, Boylan M, Piedmonte M R, Lytle B W, Loop FD. Atheroembolism from the ascending aorta. J Thorac Cardiovasc Surg 103:110–412, 1992.
4. Tuman K J, McCarthy R J, Najafi H, Ivankovich A D. Differential effects of advanced age on neurologic and cardiac risks of coronary artery operations. J Thorac Cardiovasc Surg. 104:1510–7, 1992.
5. Hosoda Y, Watanabe M, Hirooka Y, Ohse Y, Tanaka A, Watanabe T. Significance of atherosclerotic changes of the ascending aorta during coronary bypass surgery with intraoperative detection by echocardiography. J Cardiovasc Surg. 32:301–6, 1991.
6. Davila-Roman V G, Barzilai B, Wareing T H, Murphy S F, Schechtman K B, Kouchoukos N T. Atherosclerosis of the ascending aorta. 1994. Stroke 25:2010–16, 1994.
7. Barzilai B, Marschall W C Jr, Saffitz J E, Kouchoutos N. Avoidance of embolic complications by ultrasonic characterization of the ascending aorta. Circulation. 80(suppl I):I-275–79, 1989.
8. Marschall W G, Barzilai B, Kouchoukos N T, Saffitz J. Intraoperative ultrasonic imaging of the ascending aorta. Ann Thor Surg. 48:339–44, 1989.
9. Katz E S, Tunick P A, Rusinek H, et al. Protroding aortic atheromas predict stroke in elderly patients undergoing cardiopulmonary bypass: experience with intraoperative transesophageal echocardiography. J Am Coil Cardiol 20:70–7, 1992.
10. Landymore R, Kinley C E. Classification and management of the diseased ascending aorta during cardiopulmonary bypass. J Thorac Cardiovasc Surg. 85:639–40, 1983.
11. Wareing T H, Davila-Roman V C, Barzilai B, Murphy S, Kouchoukos N T. Management of the severely atherosclerotic ascending aorta during cardiac operations. J Thorac Cardiovasc Surg. 103:453–62, 1992.
12. Seward J B, Khandheria B K, Tajik J, Wide-field transesophageal echocardiographic tomography: Feasibility Study. Mayo Clin Proc. 65:31–37, 1990.
13. Konstadt S N, Reich D L, Quintana C, Levy M. The ascending aorta: how much does transesophageal echocardiography see? Anesth Analg. 78:240–244, 1994.
14. Sylviris et al. The intraoperative assessment of ascending aortic atheroma: Epiaortic imaging is superior to both transesophageal echocardiography and direct palpation. J Cardiothorac Vasc Anesth 11:704–7, 1997.
15. Kanchuger M, Tissot M, Grossi E, Armstrong J M, Marschall K. Epiaortic ultrasonography is superior to biplane transesophageal echocardiography or surgical palpation in detecting ascending aortic atherosclerosis. Abstract A110. Anesthesiology V81, No 3A, September 1994.
16. Ohteki H, Itoh T, Natsuaki M, Minato N, Suda H. Intraoperative ultrasonic imaging of the ascending aorta in ischemic heart disease. Ann Thorac Surg. 50:539–42, 1990.
17. Davila-Roman V G, Barzilai B, Wareing T H, Murphy S F, Kouchoukos N T. Intraoperative ultrasonographic evaluation of the ascending aorta in 100 consecutive patients undergoing cardiac surgery. Circulation. 84:suppl 3:47–53, 1991.
18. Karalis D G, Qinn V J, Toss J J. Transesophageal echocardiography identifies patients at high risk of arterial embolism during invasive aortic procedures. J Am Coll Cardiol. 19:280A, 1992.

I claim:

1. A hand held imaging probe for use as a diagnostic tool by an individual where said probe is held and operated in one hand by the individual, said probe comprising:
   i) a tissue contacting section containing one or more elements capable of sending to and receiving from said tissue one or more signals;
   ii) means for coupling the signals with a signal processor;
   iii) means for generating images of the tissue from processed signals from the signal processor; and
   iv) means in the probe for controlling by at least one digit of the individual at least one imaging parameter.

2. The probe of claim 1 wherein the probe is an intraoperative ultrasonic probe and the elements are ultrasonic transducers.

3. The probe of claim 2 wherein the tissue is the aorta.

4. The probe of claim 3 wherein the individual is a surgeon.

5. The probe of claim 4 wherein the means for controlling the signals is a series of finger activated switches which correspond to one or more parameters selected from the group consisting of 2D/M gain, Doppler gain, depth, output, brightness, contrast, freeze or print.

6. The probe of claim 4 wherein the means for controlling the signals is a thumb wheel rocker switch to control one or more parameters selected from the group consisting of 2D/M gain, Doppler gain, depth, output, brightness, contrast, freeze or print.

7. The probe of claim 6 wherein the means for coupling the signals with the signal processor is wireless.

8. The probe of claim 4 wherein the probe is coupled to an aspiration tube capable of atraumatic insertion into the chambers of the heart.

9. The probe of claim 8 wherein the tube is silastic tubing.

10. The probe of claim 4 wherein a scanning probe offset is located between the surface of the probe which contacts tissue and the tissue.

11. The probe of claim 10 wherein the offset is saline-filled and has an acoustically dense grid.

12. The probe of claim 2 wherein the ultrasound transducers can function alternately in Doppler or B-mode.

13. A hand held imaging intraoperative ultrasonic probe for use by a surgeon as a diagnostic tool where said probe is held and operated in one hand of the surgeon, said probe comprising:
   i) a tissue contacting section containing one or more ultrasonic transducers capable of sending to and receiving from the tissue one or more signals;
   ii) means for coupling the signals with a signal processor;
   iii) a video display terminal for generating images of the interior of the tissue from processed signals from the signal processor; and
   iv) means in the probe for controlling by a digit of the surgeon at least one imaging parameter.

14. The probe of claim 13 wherein the means in the probes for controlling is a thumb wheel rocker switch which controls 2D/M gain, Doppler gain, depth, output, brightness, contrast, freeze and print functions.

15. The probe of claim 14 wherein the tissue is the aorta.

16. A method for producing an ultrasonic image of the interior of vasculature comprising:
   i) contacting an ultrasonic transducer section of a hand held intraoperative ultrasonic imaging probe to the vasculature;
   ii) causing the transducer to send to and receive from the vasculature one or more signals;
   iii) coupling the signals with a signal processor;
   iv) displaying at least one image of the interior of the vasculature generated from processed signals from the signal processor; and
   v) controlling by controlling means of the probe at least one imaging parameter.

17. The method of claim 16 wherein the vasculature is the aorta.

18. The method of claim 17 wherein the parameter is selected from the group consisting of 2D/M gain, Doppler gain, depth, output, brightness, contrast, freeze or print.

19. The method of claim 18 wherein the controlling means is selected from the group consisting of a thumb wheel rocker switch and individual finger switches.

20. The method of claim 18 wherein the signals are coupled with the signal processor by a wireless connection.

21. The method of claim 18 wherein the probe is coupled to an aspiration tube capable of atraumatic insertion into the chambers of the heart.

22. The method of claim 18 wherein a scanning probe offset is located between the surface of the probe which contacts tissue and the tissue and the offset is saline-filled and has an acoustically dense grid on its surface.

23. A hand held imaging probe for use as a diagnostic tool by an individual where said probe is held in one hand by the individual, and is controlled through a unit attached to the individual, said unit comprising:
   i) means for coupling signals from the probe with a signal processor;
   ii) means for generating images of the tissue from processed signals from the signal processor; and
   iii) means in the unit for controlling by at least one digit of the individual at least one imaging parameter.

* * * * *